United States Patent [19]
Bennett

[11] Patent Number: 5,804,715
[45] Date of Patent: Sep. 8, 1998

[54] HYDRODYNAMIC DAMPENING SYSTEM FOR THE PRECISE MEASUREMENT OF DYNAMIC SEDIMENT PORE WATER PRESSURE

[75] Inventor: Richard H. Bennett, Carriere, Miss.

[73] Assignee: The United States of America as represented by the Secretary of the Navy, Washington, D.C.

[21] Appl. No.: 773,290

[22] Filed: Dec. 24, 1996

[51] Int. Cl.⁶ ................................................. G01L 13/00
[52] U.S. Cl. ......................... 73/170.32; 73/38; 73/866.5
[58] Field of Search .................................. 73/38, 170.29, 73/170.32, 170.34, 707, 866.5, 706, 736, 756

[56] References Cited

U.S. PATENT DOCUMENTS

| | | | |
|---|---|---|---|
| 3,534,605 | 10/1970 | De Koning et al. ................. | 73/170.34 |
| 3,935,745 | 2/1976 | Jonell et al. ................. | 73/38 |
| 4,150,578 | 4/1979 | Swartz ........................ | 73/38 |
| 4,332,172 | 6/1982 | Torstensson ................. | 73/707 |
| 4,445,788 | 5/1984 | Twersky et al. ........................ | 73/866.5 |
| 4,517,842 | 5/1985 | Twomey et al. .......................... | 73/701 |
| 4,984,447 | 1/1991 | Phillips ........................ | 73/38 |

*Primary Examiner*—Ronald L. Biegel
*Attorney, Agent, or Firm*—Thomas E. McDonnell; Barry A. Edelberg

[57] ABSTRACT

A multi-sensor piezometer is disclosed that includes a shaft and an upper chamber. The shaft houses a plurality of porous stones that operatively cooperate with the positive input of respective differential pressure transducers. The multi-sensor piezometer further includes a hydraulic dampening system which eliminates the effect of high frequency surface waves on the precision of the multi-sensor piezometer to measure pore pressures in marine sediments.

10 Claims, 8 Drawing Sheets

HYDRODYNAMIC DAMPENING SYSTEM FOR THE PRECISE MEASUREMENT OF DYNAMIC SEDIMENT PORE WATER PRESSURE

BACKGROUND OF THE INVENTION

1.0 Field of the Invention

The present invention relates to a piezometer for measuring the water pressure in marine sediments and, more particularly, to a piezometer having dampening means to enable the measurement of the pore water pressures while compensating for the slow thermal and mechanical kinetic energy changes that occur at time intervals commonly observed for tidal cycles of low amplitude and having accompanying temperature changes.

2.0 Description of the Prior Art

Understanding and obtaining sediment pore pressure measurements in marine shallow water deposits is important but is somewhat limited by the effects of water advection. Water is advected in coastal environments under the action of surface waves, tides, and stresses on the interface of the sea floor. These stresses are transmitted through the sediments and result in changes in effective stress and pore water pressure which can lead to: loss of sediment strength resulting in under water slides (slumps); changes in bearing capacity; changes in shear modulus; and changes in acoustic wave propagation characteristics. These effective stress and pore water pressure changes can also enhance the potential for sediment transport along the sea floor and can cause fluid flow across the sediment/water interface. The cyclic loading of the marine sediments under the action of surface waves results in a pumping of fluids into and out of the sediment/water interface, termed ventilation, and more fully disclosed in the technical article "Field Observations of the Fluid-Grandular Boundary Layer Under Near-Breaking Waves," published in *Journal of Geophysical Research*, Vol. 97, No. C6, June 1992, pp. 9631–9643, the entirety of which is incorporated herein by reference for all purposes. Other submarine processes that need to be measured and that can produce pore pressure changes and induce excess pore water pressures ($u_c$ pressure in excess of the hydrostatic pressure) include: high sedimentation rates in low permeability soils resulting in underconsolidation; shearing and deformation during cyclic loading and/or net directional loading, production of in situ gas; induced thermal gradients; penetration of objects into normally or underconsolidated deposits; seismic shock waves; osmotic pressure changes; and artesian conditions.

Geotechnical engineers and marine geologists have long recognized the importance of understanding the fundamental mechanisms that govern the generation of sediment pore pressures and that determine the dynamic behavior of marine sediments in response to surface wave activity in coastal environments and such recognition is disclosed in the technical articles of Henkel, D. J., "The Role of Waves in Causing Submarine Landslides," published in *Geotechnique*, Vol. 20, No. 1, 1970, pp. 75–80; Wright, S. G. and Dunham, R. S., "Bottom Stability Under Wave Induced Loading," published in *Offshore Technology Conference*, paper 1603, May 1–3 1972, Houston, Tex.; Mitchell, R. J., Tsui, K. K., and Sangrey, S. A., "Failure of Submarine Slopes Under Wave Action," published in *Coastal Engineering*, Vol. 11, Ch. 84, pp. 1516–1541, proceedings of the Thirteenth Coastal Engineering Conference, July 10–14, 1972; Bea, R. G. and Arnold, P., "Movements and Forces Developed by Wave-Induced Slides in Soft Clays," published as Paper Number 1899 in *Offshore Technology Conference*, 1973; Bennett, R. H., Bryant, W. R., Dunlap, W. A., and Keller, G. H., "Initial Results and Progress of the Mississippi Delta Sediment Pore Water Pressure Experiment," published in *Marine Geotechnique*, Vol. 1, 1975, pp. 327–355; and Bennett, R. H., Burns, J. T., Clark, T. L., Faris, J. R., Forde, E. G., and Richards, A. R., "Piezometer Probes for Assessing Effective Stress and Stability in Submarine Sediments," published in *Marine and Slides and Other Mass Movements*, Saxon, J. and J. K. Nieuwenbuis (editors), Plenum Press, New York, 1982, pp. 129–161; the entirety of all of the above mentioned technical articles is incorporated by reference for all purposes. While significant work has been performed both on theoretical modeling (focusing principally on poroewstic solutions) and on field measurements, a fundamental understanding of the principal mechanisms that control pore pressure generation under surface wave activity is still somewhat lacking, but its obtainment could be eased by a multi-sensor piezometer that accurately and reliably measures sediment pore water pressures below the floor of the sea.

Perhaps the earliest attempt to measure sediment pore water pressures in a deep marine environment was conducted by Richards et al in the Wilkinson Basin and described in the technical article "Differential Piezometer Probe for an In-Situ Measurement of Sea Floor Pore Pressure," published in *Geotechnique*, Vol. 25, No. 2, 1975, pp. 229–238, the entirety of which is incorporated herein by reference for all purposes. Their technique used a vibrating wire concept developed by the Norwegian Geotechnical Institute. During the 1970's several piezometers were deployed in the Mississippi Delta to assess the presence of ambient pore water pressures in soft marine deltaic deposits, to monitor long-term changes in pore water pressure, and to measure dynamic pore water pressure being driven by wave-induced bottom pressures during severe weather conditions as more fully described in the two (1975 and 1982) previously mentioned technical articles of Bennett et al, and also in the two technical articles of Hirst, T. J. and Richards, A. F., "Excess Pore Pressure in Mississippi Delta Front Sediments Initial Report," published in *Marine Geotechnology*, Vol. 1, 1976; and Dunlap, W. A., Bryant, W. R., Bennett, R. H. and Richards, A. F., "Pore Pressure Measurements in Underconsolidated Sediments," disclosed at *Offshore Technology Conference*, 10th Annual Meeting, May 8–11, 1978, Houston, Tex.; the entirety of both technical articles being incorporated by reference for all purposes. Highly sensitive piezometer probes (−0.07 kPa precision) have been developed to operate at full ocean depths (5000 m) in soft clays for the principal purpose of monitoring the in-situ pore water pressures induced by thermal gradients that would develop should radioactive material be placed in seafloor sediments, and are more fully described in the technical articles of Bennett, R. H., Burns, J. T., Nastav, F. L., Lipkin, J., and Percival, C. M., "Deep Ocean Piezometer Probe Technology for Geotechnical Investigations," published in *IEEE Journal of Oceanic Engineering*, Vol. OE-10, No. 1, invited paper, 1985, pp. 11–22, the entirety of which is incorporated herein by reference for all purposes; Bennett, R. H., Li, H., Burns, J. T., Percival, C. M., and Lipkin, J., "Application of Piezometer Probes to Determine Engineering Properties and Geological Processes in Marine Sediments," published in *Applied Clay Science*, Vol. 4, Elsevier Science Publishers, B. V. Amsterdam, Netherlands, 1989, pp. 337–355, the entirety of which is incorporated herein by reference for all purposes; and Bennett, R. H., Burns, J. T., Li, H., Walter, D., Valent, P. J., Percival, C. M., and Lipkin, J., "Subseabed Disposal Project Experiment: Piezometer Probe Measurement Technology," K. Remers and R. Chaney, eds., "Geotechnical Engineering of Ocean Waste Disposal," published in *American Society for Testing Materials. Standard Technical Publication* 1087, 310 pp. 1990, pp. 175–189, the entirety of which is incorporated herein by reference for all purposes. These deep water probes have been modified to operate from a tethered configuration for multiple insertions in oceanic environments as more fully disclosed in the technical article of Davis, E E., Horel, G. C., MacDonald, R. D., Villinger, H., Bennett, R. H., and Li, H., "Pore Pressures and Permeabilities Measured in Marine Sediments with a Tethered Probe," published in *Journal of Geophysical Research*, Vol. 96, No. B4, April 1991, pp. 5975–5984, the entirety of which is incorporated herein by reference for all purposes.

Although these earlier instruments serve well their intended purpose and measure dynamic sediment pore water pressures using absolute or gauge pressure transducers and differential pressure transducers, these systems are limited considerably by the accuracy and precision of the sensors as a function of total stress when measuring short period low amplitude wave affects. The differential transducers used in these earlier instruments do not have a hydrodynamic dampening system as part of a device commonly referred to as pore water pressure probe or piezometer probe. Thus, the differential transducers although having a high overall precision do not measure or compensate for the wave affects and, thus, their accuracy is somewhat degraded. It is desired to provide a piezometer probe and arrays thereof that have a hydrodynamic dampening system that enables the precise measurement of low amplitude, short period, wave-induced bottom and sub-bottom pressures in marine sediments.

OBJECTS OF THE INVENTION

Accordingly, it is a primary object of the present invention to provide a piezometer probe having a hydrodynamic dampening system that enables the precise measurement of bottom and sub-bottom pressures in spite of any wave induced forces.

It is another object of the present invention to provide a piezometer in the form of a multi-sensor device having a hydrodynamic dampening system that may be arranged into waves which find application in systems for the collections of geotechnical and environmental data.

Furthermore, it is an object of the present invention to provide a multi-sensor piezometer having a hydrodynamic dampening system that dampens out the effects of pressure waves that would normally be sensed by the multi-sensor piezometer.

In addition, it is an object of the present invention to provide calibration and operational processes that allow for the easy deployment of the multi-sensor piezometer of the present invention.

SUMMARY OF THE INVENTION

The present invention is directed to a multi-sensor piezometer having a hydrodynamic system for dampening the effects of surface waves that would otherwise effect the precise measurements of the pore water pressures in marine sediments.

The piezometer comprises a tubular shaft, a first chamber, a plurality of pressure transducers, a fluid having a density greater than sea water, a pocket of sea water, first and second porous stones, and a pocket of air. The tubular shaft has one end that is tapered and houses the plurality of first porous stones that are spaced apart from each other by a first distance and connected to one end of a tube. The first chamber is connected to the other end of the tubular shaft and has entrance portions. The plurality of differential pressure transducers are housed in the first chamber and assigned one for each of the first porous stones and each has positive and negative pressure inputs that provide an output signal proportional to the difference between the positive and negative pressure inputs. Each of the plurality of differential transducers has its positive input connected to the other end of the tube of its respective first porous stone. The fluid having a density greater than sea water is of a sufficient amount to immerse the plurality of differential pressure transducers. The second porous stones are disposed in the entrance portions of the first chamber and are adapted to allow sea water to enter therethrough to form a pocket of sea water floating on the fluid within the first chamber. The pocket of air is confined in the first chamber and is trapped above the pocket of sea water.

BRIEF DESCRIPTION OF THE DRAWINGS

These and other objects, features and advantages of the invention, as well as the invention itself, will become better understood with reference to the following detailed description when considered in connection with the accompanying drawings, where like reference numbers designate identical or corresponding parts throughout the several views and wherein.

DETAILED DESCRIPTION OF THE PREFERRED EMBODIMENTS

Figure 1:
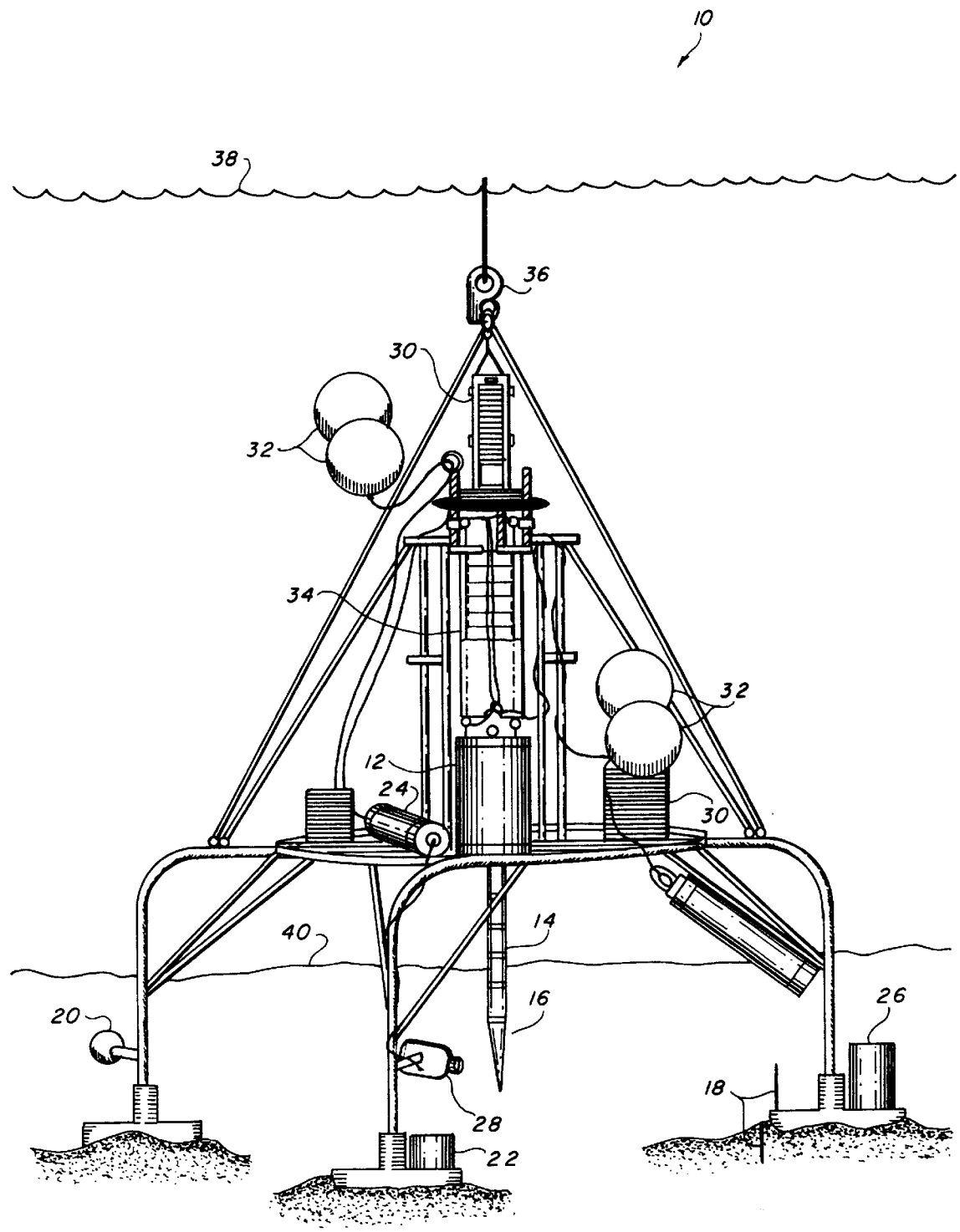
FIG. 1 is a schematic diagram of Seafloor Lander System employing the multi-sensor piezometer of the present invention.

With reference to the drawings, there is shown in FIG. 1 a Seafloor Lander system 10 in which the practice of the present invention may be applied. The Seafloor Lander system 10 includes a multi-sensor piezometer 12 having a probe 14 that has means for lodging spaced-apart porous stones 16, and instrumentation, such as temperature probes 18, for measuring temperature of bottom water and surficial sediment. The Seafloor Lander system 10 further includes a current meter 20 for measuring current speed and a heading sensor 22 for measuring Lander orientation, known in the art. The Seafloor Lander system 10 also includes an on-board data acquisition system 24, power supplies 26, cameras 28, and acoustic releases 30 for deployment and recovery. The Seafloor Lander system 10 further carries floats 32, driving weights 34 that are removable, and a electro-mechanical release means 36. The Seafloor Lander system 10 is lowered below the sea level 38 and causes the piezometer probe 14 of the multi-sensor piezometer 12 to be inserted into marine sediments 40.

The multi-sensor piezometer 12 is of primary importance to the present invention and provides measurement and long term monitoring of near surface marine sediment ambient and dynamic pore water pressures. The multi-sensor piezometer 12 provides measurements of pore water pressures in marine sediments which are essential to understanding the mechanisms that can result in the loss of shear strength thereof, and are essential to predicting the movements of contaminants in and out of the marine sediments 40. The multi-sensor piezometer 12 is further described with reference to FIG. 2.

Figure 2:
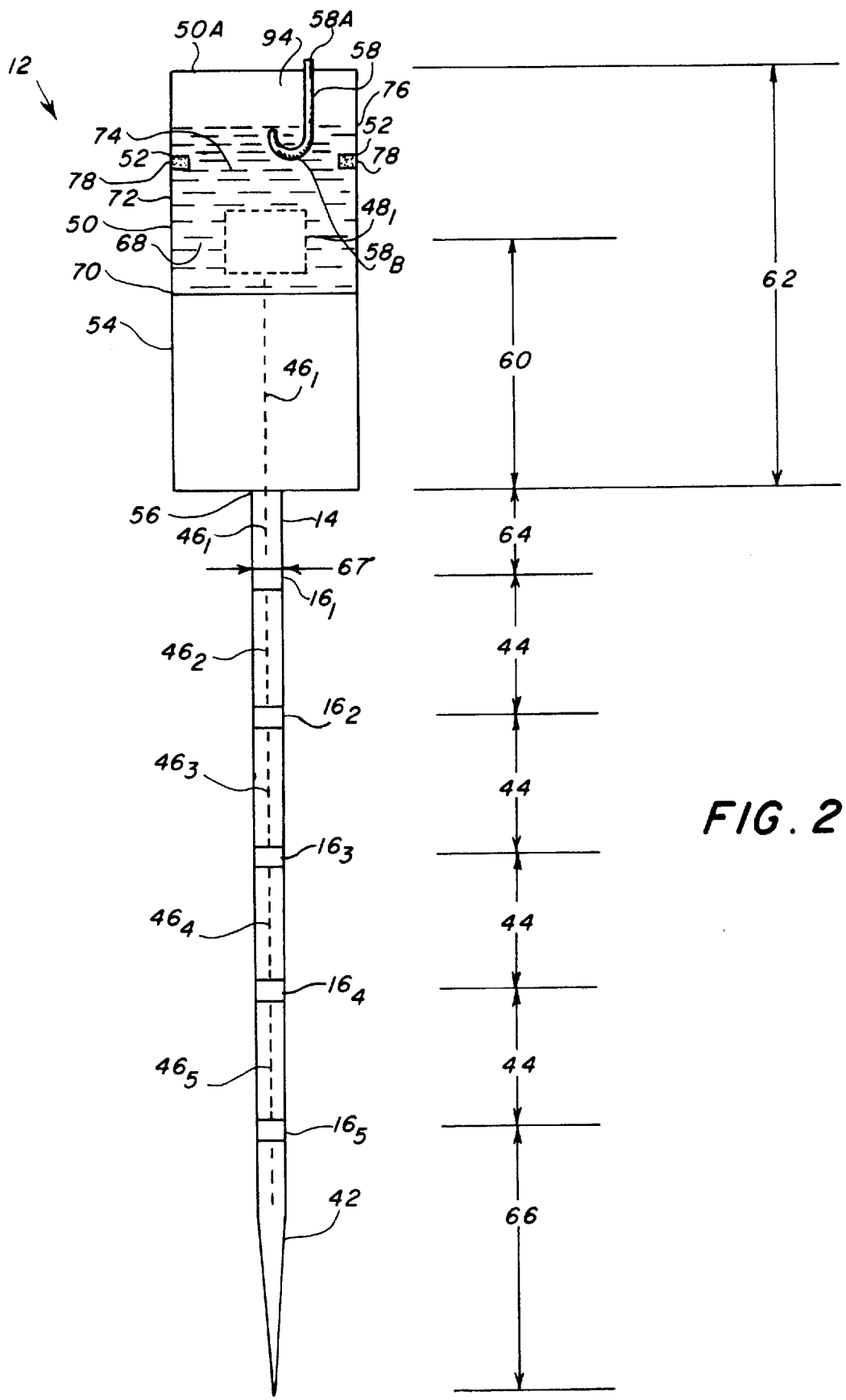
FIG. 2 is a schematic diagram of multi-sensor piezometer illustrating the distances to porous stone locations from the neutral axis of the differential pressure transducers.

FIG. 2 illustrates the probe 14 of the multi-sensor piezometer as being a tubular shaft having one end 42 that is tapered so as to be inserted into the marine sediment. The probe 14 houses porous stones 16, shown in FIG. 2 as comprising a plurality of first porous stones $16_1, 16_2, 16_3, 16_4, 16_5$ that are spaced apart from each other by a predetermined distance 44 which may have a typical value of 0.208 meters (m). The porous stones $16_1, 16_2, 16_3, 16_4$ and $16_5$ accept respectively, one end of tubes $46_1, 46_2, 46_3, 46_4,$ and $46_5$ (shown in phantom). The other end of the tubes $46_1, 46_2, 46_3, 46_4,$ and $46_5$ are respectively connected to differential pressure transducers $48_1, 48_2, 48_3, 48_4, 48_5$ (shown in phantom). Only the tube $46_1$ and the differential pressure transducer $48_1$ are shown in FIG. 2. The differential pressure transducers $48_1, 48_2, 48_3, 48_4, 48_5$ are housed in a first chamber 50 having entrance portions 52. Preferably the multi-sensor piezometer 12 comprises a second chamber 54 having predetermined dimensions that are complementary to predetermined dimensions of the first chamber 50 and is interposed between the first chamber 50 and the other end 56 of the probe 14. The first chamber 50 has a top portion 50A having an entrance portion (not shown) that allows for the insertion of a relief valve 58 having an entrance portion 58A open to ambient and an exit portion 58B.

Each of the differential pressure transducers $48_1, 48_2, 48_3, 48_4,$ and $48_5$, has a neutral axis (to be further described with reference to FIG. 3) that is located at a distance 60 from the end 56 of the probe 14 having a typical value of 0.540 m. The overall length 62 of the first chamber 50 and the second chamber 54 has a typical value of 0.750 m. A distance 64 measured from the end 56 of shaft 14 to the location of the first porous stone $16_1$ has a typical value 0.10 m, and the end 42 of the probe 14 has an overall length 66, measured from the location of the first porous stone $16_5$ to the end tapered so as to be inserted into the sediment, having a value of 0.513 m, and the tapered end 42 has a cone angle of about 5.3°.

The probe 14 has an overall length of about 1.5 m and a diameter 67 of 0.025 m, and is typically composed of a stainless steel material such as Nitronic 50 or other strong wear and corrosion-resistant material.

The five porous stones $16_1, 16_2, 16_3, 16_4$ and $16_5$ are preferably comprised of a fused aluminum oxide having a pore size of about 0.26 mm and within a range from about 0.23 mm to about 0.29 mm, a permeability from about 1.7 to about $2.0 \times 10^{-1}$ cm/sec, and a porosity of about 35% to 40%. Each of the stones $16_1, 16_2, 16_{3,} 16_4$ and $16_5$ is hydraulically and separately connected through a 3.2 mm outside diameter stainless steel tube $46_1, 46_2, 46_3, 46_4,$ and $46_5$ to respectively establish fluid communications therebetween. The other end of the tubes $46_1, 46_2, 46_3, 46_4,$ and $46_5$ are respectively connected to the positive port, sometimes referred to as side, input of the differential pressure transducers $48_1, 48_2, 48_3, 48_4,$ and $48_5$.

Each of the differential pressure transducers $48_1, 48_2, 48_3, 48_4,$ and $48_5$ has provisions (not shown but known in the art) for being mounted inside the upper chamber 50 and has a positive port having a characteristic of ±34.4 kPa (5 psi) and has a variable reluctance characteristic. These five variable reluctance differential pressure transducers $48_1, 48_2, 48_3, 48_4,$ and $48_5$ may be manufactured by Validyne (Model P305) with a full-scale output of ±5 volts in response to DC excitation voltages ranging from 11 to 30 volts, and preferably have an over pressure rating of 100%. Each of the differential pressure transducers $48_1, 48_2, 48_3, 48_4,$ and $48_5$ is immersed in a fluid 68 shown in FIG. 1 as having a lower boundary 70 (shown in solid) and an upper boundary 72 (shown in phantom).

The fluid 68 is preferably a type commercially distributed by 3M having a trade name of Fluorinert FC-40 which is dense (greater than sea water) and serves as an inert instrumentation fluid having a very low surface tension (16 dynes/cm) and a low viscosity (2.4 centistokes). The fluid 68, being heavier than sea water displaces sea water 74, shown in FIG. 2, from the lower section of chamber 50, thus protecting all of the differential pressure transducers $48_1, 48_2, 48_3, 48_4,$ and $48_5$ from corrosion. As will be further described, the negative ports or sides of the differential pressure transducers $48_1, 48_2, 48_3, 48_4,$ and $48_5$ are open to the fluid 68.

The sea water 74 floating on the fluid 68 has a lower boundary 72 shared with the fluid 68 and an upper boundary 76. The sea water 74 enters the chamber 50 by way of entrance portions 52 which has lodged therein second porous stones 78 that are preferably comprised of high air entry (HAE) stones, known in the art. The exit portion 58B of the relief valve 58 empties into the sea water 74. Further details of the parameters of the sea water 74 and the upper chamber 50 may be further described with reference to FIG. 3 which illustrates the upper chamber 50 as being devoid of the relief valve 58.

Figure 3:
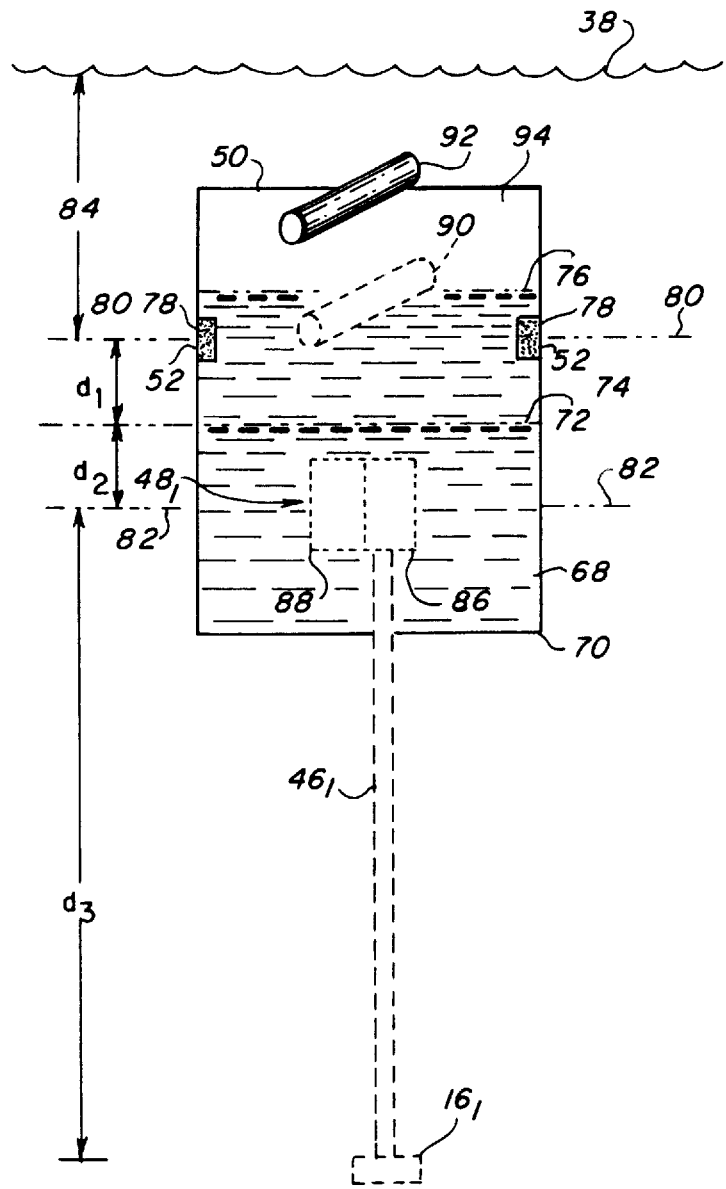
FIG. 3 is a schematic diagram of the upper chamber of the multi-sensor piezometer housing the dampening system of the present invention.

FIG. 3 illustrates the HAE porous stones 78 located in the entrance portions 52 of the chamber 50 as having a centerline 80. FIG. 3 also illustrates the plurality of differential pressure transducers $48_1, 48_2, 48_3, 48_4,$ as having a neutral axis 82 (previously mentioned with reference to FIG. 2). The distance from the centerline 80 to the surface of the water 38 is shown in FIG. 3 by dimension line 84, whereas the distance of the centerline 80 to the boundary 72 which is a common interface between the sea water 74 and the fluid 68 is shown by a distance $d_1$. The distance from the boundary 72 to the neutral axis 82 is shown by a distance $d_2$, whereas the distance from the neutral axis 82 to the first porous stone $16_1$ is shown by a distance $d_3$. The distances 84, $d_1$, $d_2$, and $d_3$ serve as a datum for the establishment of a reference pressure for each of the differential pressure transducers $48_1, 48_2, 48_3, 48_4$ and $48_5$. Each of the differential pressure transducers $48_1, 48_2, 48_3, 48_4$ and $48_5$ have a positive pressure input or side 86 (previously discussed) and a negative pressure input or side 88. Each of the differential pressure transducers, such as differential pressure transducer $48_1$ shown in FIG. 3, has its positive input or positive side 86 operatively connected to its associated porous stone $16_1$ and its negative pressure input or negative side 88 open to the fluid 68 which preferably is comprised of Fluorinert.

The upper chamber 50 further comprises mounts for two total pressure transducers 90 and 92 both of which may be manufactured by Keller PSI (Model PAA-9) with an active range of 0–200 kPa. The total pressure transducer 90 (shown in phantom), is mounted inside the chamber 50, whereas the total pressure transducer 92 is mounted outside the chamber 50. Both total transducers 90 and 92 have full-scale outputs of ±5 volts in response to DC excitations ranging from 11 to 30 volts. The chamber 50 has provisions for accommodating a sixth differential pressure transducer $48_6$ (not shown) so as to be connected through the top of the chamber 50 to a free water column and, as will be further described, serves as a redundant measurement of sea water column pressure.

In general, each of the differential pressure transducers $48_1$, $48_2$, $48_3$, $48_4$ and $48_5$ functions as a manometer in sensing differences in pressure between the column of fluid 68 (Fluorinert) on the positive side 86 of each of the differential pressure transducers $48_1$, $48_2$, $48_3$, $48_4$ and $48_5$ respectively connected to the porous stones $16_1$, $16_2$, $16_3$, $16_4$ and $16_5$, and the pressure inside the chamber 50 as sensed at the negative side 88 of each of the differential pressure transducers $48_1$, $48_2$, $48_3$, $48_4$ and $48_5$.

In operation, an air pocket 94, shown in both FIGS. 2 and 3, is trapped above the upper boundary 76 of the sea water 74 which, in turn, is floating on the fluid 68 in the chamber 50. The high air entry (HAE) porous stones 78 are mounted in the entrance portions 52 of chamber 50 at the level of sea water and in a manner to allow the HAE porous stones 78 to slowly transmit or transfer sea water into and out of the chamber 50 (the rate of transmission depends upon the permeability selected for the HAE porous stones). The air pocket 94 located above the sea water 74 in chamber 50 acts in conjunction with the preferably low permeability HAE porous stones 78 to create an efficient dampening mechanism that filters out the surface wave (see FIG. 1) effects on the negative side 88 of the differential transformers $48_1$, $48_2$, $48_3$, $48_4$ and $48_5$, allowing only the positive side 86 of the differential transformers $48_1$, $48_2$, $48_3$, $48_4$ and $48_5$, respectively having fluid communication with porous stones $16_1$, $16_2$, $16_3$, $16_4$ and $16_5$ inserted in the marine sediment 40 (see FIG. 1), to respond to these high frequency events created by the surface wave effects.

The two total pressure transducers 90 and 92 are arranged so that the total pressure transducer 90 mounted inside the chamber 50 provides a reference measurement for the negative side pressure thereof permitting the assessment of the behavior of the cyclic pressure dampening system of the present invention essentially comprising the fluid 68, the sea water 74, the HAE stones 78 and the air pocket 94. The second total pressure transformer 92 mounted on the outside of chamber 50 is operatively placed in a free water column of the sea. The positive side of the sixth differential pressure transformer $48_6$, connected through the top of the chamber 50 to the free water column, serves as a redundant measurement of sea water column pressure. In one typical operation, during the deployment of the multi-sensor piezometer 12 of the present invention, as it was lowered through the water column, the valve 58 mounted on the top of the upper chamber 50 was opened to allow for a rapid equilibrium on the inside of the chamber 50 so as to bypass the operation of HAE stones 78 in order to prevent an overloading of the differential pressure transducers $48_1$, $48_2$, $48_3$, $48_4$, and $48_5$. If desired, two pressure relief valves (typically about 34.4 kPa), similar to relief valve 58, may be placed through the sides of the upper chamber 50 as a redundant pressure overload system. The information or pressure sensed by all of the differential pressure transducers $48_1$, $48_2$, $48_3$, $48_4$, $48_5$, be gathered and analyzed by the data acquisition system 24 which may be further described with reference to FIG. 4.

Figure 4:
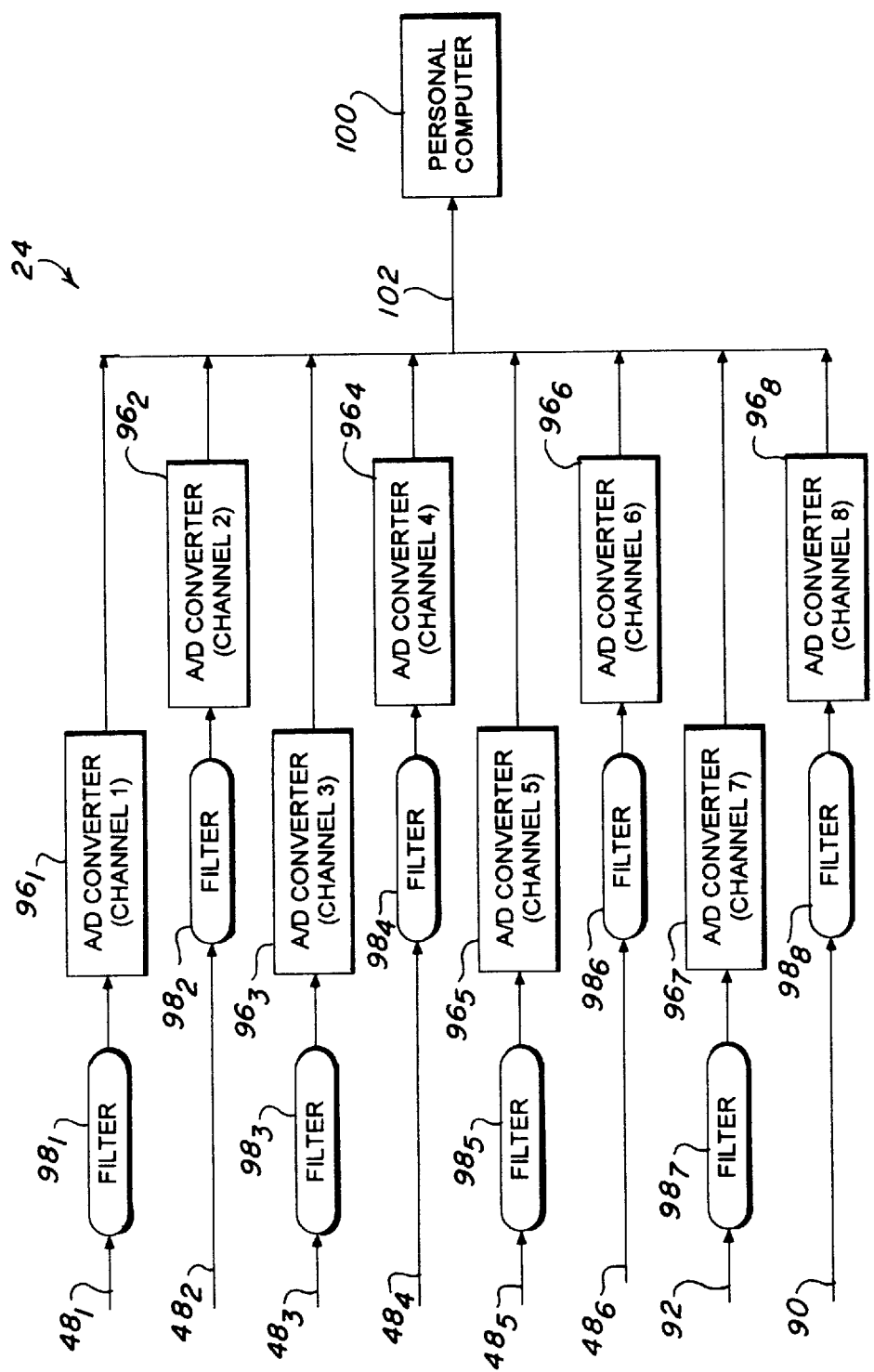
FIG. 4 is a block diagram of a data acquisition system that may be used in the practice of the present invention.

FIG. 4 illustrates the data acquisition system 24, previously mentioned with regard to FIG. 1, comprising two 12-bit 8-channel A/D converters $96_1$, $96_2$, $96_3$, $96_4$, $96_5$, $96_6$, $96_7$, and $96_8$, respectively having at their input stage band-limit filters $98_1$, $98_2$, $98_3$, $98_4$, $98_5$, $98_6$, $98_7$, and $98_8$. Each of the A/D converters $96_1$, $96_2$, $96_3$, $96_4$, $96_5$, $96_6$, $96_7$, and $96_8$, respectively serving as channel 1, channel 2, channel 3, channel 4, channel 5, channel 6, channel 7, and channel 8, may be, for example, a Tattletale Model 6 unit manufactured by Onset Computer Corp., with sampling rates up to 10 Hz. The maximum sampling delay channel-to-channel for this Model 6 unit is $3 \times 10^{-6}$ seconds. The filters $98_1$, $98_2$, $98_3$, $98_4$, $98_5$, $98_6$, $98_7$ and $98_8$, may each, for example in cooperation with the Model 6 unit, be of an eighth-order, low-pass, Butterworth anti-alising filter with cutoff frequencies of 4 Hz and preferably receive their input signal by means of an Impulse connector, known in the art. Each of the A/D converters $96_1$, $96_2$, $96_3$, $96_4$, $96_5$, $96_6$, $96_7$, and $96_8$, preferably has a 200 Mbyte, or larger, hard drive for remote data storage and each may communicate with a personal computer 100 by way of a communicate bus 102 which may be, for example, a RS-231 serial configuration having a baud rate of 19,200 or higher. The associated data can be stored in real time on a hard drive.

In one application related to the present invention shown in FIG. 4, the A/D converters $96_1$, $96_2$, $96_3$, $96_4$, $96_5$, $96_6$, $96_7$, and $96_8$ respectively acting as channels 1, 2, 3, 4, 5, 6, 7 and 8, are respectively arranged to receive the outputs of the transducers $48_1$, $48_2$, $48_3$, $48_4$, $48_5$, $48_6$, 92 and 90. During a typical deployment of the multi-sensor piezometer 12, each pressure transducer is recorded in terms of channel number as recognized by the data acquisition 24, and by the appropriate active depth below the sea floor corresponding to sediment 40 (shown in FIG. 1) and the results of a typical deployment are given in Table 1.

TABLE 1

| Channel Number | Transducer Type | Location of Measured Pressure | Approximate Distance Below Sea Floor (m) |
|---|---|---|---|
| 1 | Differential ($48_1$) | Porous stone ($16_5$) closest to the insertion tip of the probe shaft | 0.93 |
| 2 | Differential ($48_2$) | Next highest porous stone ($16_4$) on shaft | 0.72 |
| 3 | Differential ($48_3$) | Next highest porous stone ($16_3$) on shaft | 0.52 |
| 4 | Differential ($48_4$) | Next highest porous stone ($16_2$) on shaft | 0.31 |
| 5 | Differential ($48_5$) | Porous stone ($16_1$) closest to sea floor sediment surface | 0.10 |

TABLE 1-continued

| Channel Number | Transducer Type | Location of Measured Pressure | Approximate Distance Below Sea Floor (m) |
|---|---|---|---|
| 6 | Differential ($48_6$) | Free water column on top of the probe housing | −0.75 |
| 7 | Absolute (92) | Free water column outside the upper chamber 50 | −0.05 |
| 8 | Absolute (90) | Sea water (74) pocket inside upper chamber 50 | −0.65 |

In the practice of this invention the electrical distortion A/D channel ($96_1 \ldots 96_8$ (see FIG. 4)) due to signal ng) was measured with an HP model 61148 precision power supply and an HP model 3478A high performance digital voltmeter with 1/300,000 precision. During this measurement with the related transducers disconnected, the applied voltage was cycled twice from −4 to +4 volts on each channel ($96_1 \ldots 96_8$) and a linear regression analysis was performed on the resulting data to develop calibration equations of the following form:

$$V_a = C_{f1}V_m + V_o \quad (1)$$

where $V_a$ is the actual voltage applied to each channel, $V_m$ is the measured voltage, $C_{f1}$ is the calibration factor (slope of the regression line) and $V_o$ is the zero shift. These equations are incorporated directly into the data acquisition program residing in the personal computer 100 so that the raw data are corrected for the electronic distortion in real time. Table 2, given below, summarizes these calibration equations in terms of the calibration factor and the y-intercept along with the $r^2$ value for each channel.

TABLE 2

Calibration Equation $V_a = C_{f1}V_m + V_o$

| Channel Number | Calibration Factor $C_{f1}$ (unitless) | Zero Shift $V_o$ (Volts) | $r^2$ |
|---|---|---|---|
| 1 ($96_1$) | 0.9944 | 0.0123 | 1.0000 |
| 2 ($96_2$) | 0.9976 | 0.0041 | 1.0000 |
| 3 ($96_3$) | 0.9896 | 0.0042 | 1.0000 |
| 4 ($96_4$) | 0.9987 | 0.0041 | 1.0000 |
| 5 ($96_5$) | 1.0107 | 0.0171 | 1.0000 |
| 6 ($96_6$) | 0.9969 | 0.0043 | 1.0000 |
| 7 ($96_7$) | 1.0006 | 0.0196 | 1.0000 |
| 8 ($96_8$) | 1.0012 | −0.0093 | 1.0000 |

Operation of the Multi-Sensor Piezometer 12

In operation, the total water pressure ($P_s$) at each porous stone $16_1 \ldots 16_5$ location on the insertion probe 14 can be determined from the measured differential pressure, a reference pressure inside the chamber 50, and the geometry of the multi-sensor piezometer 12, in particular, the portion of the multi-sensor piezometer 12 illustrated in FIG. 3. Using the principles of manometry, the following equation can be developed and may be used to convert measured differential pressures into total pressures:

$$P_s = P_m + P_u + d_1\gamma_s + (d_2 + d_3)\gamma_f \quad (2)$$

where $P_m$ is the measured differential pressure, $P_u$ is the total pressure in the upper chamber 50 at the elevation of the HAE stones 78, $d_1$ is the vertical distance from the HAE stones to the top of the Fluorinert (fluid 68) inside the upper chamber 50 (constant for all differential transducers and for a given deployment and having a typical value equal to 0.0508 m) $d_2$ is the depth of the Fluorinert (fluid 68) on the negative side 88 of the differential transducers $48_1 \ldots 48_6$ to the neutral axis 82 of the differential transducers $48_1 \ldots 48_5$ (constant for all differential transducers and for a given deployment having a typical value equal to 0.041 m), $d_3$ is the distance from the neutral axis 82 of the differential transducers $48_1 \ldots 48_5$ to the corresponding porous stone ($16_1 \ldots 16_5$) on the probe 14 (shown in FIG. 2), and $\gamma_s$ is the unit weight of sea water (1.02 g/cc) and $\gamma_f$ is the unit weight of Fluorinert (1.86 g/cc at 25° C.). Equation (2) is used to convert the measured differential pressures into total pressures. The present invention, as described with reference to FIGS. 2 and 3, includes the hydrodynamic dampening system comprising the fluid 68 (Fluorinert), sea water 74 forming a pocket, air pocket 94, and the second porous stones 78 (HAE) and it may be described with reference to the general equations that control its operation.

The pressure inside the upper chamber 50 at the level of the low permeability (HAE) stones 78 ($P_{cu}$) can be related to the sea water column pressure outside the upper chamber 50 by the following equation:

$$P_{au} = P_{awc} - \Delta P \quad (3)$$

where $P_{awc}$ is the absolute pressure in the water column outside the upper chamber 50 at the elevation (defined by centerline 80) of the low permeability HAE stones 78, and $\Delta P$ is the pressure drop across the low permeability HAE stones 78 (refer to FIG. 3). The dampening system of the present invention is intended to remove the cyclic component of $P_{awc}$ (the pressure drop across the low permeability (HAE) stones 78 is equal to the cyclic component) so that $P_{au}$ will equal the total static water column pressure, and there will be no wave effects on the negative side 88 of the differential pressure transducers $48_1 \ldots 48_6$.

In the practice of this invention, a theoretical analysis of the cyclic dampening system comprising the elements 68, 74, 78 and 94 of FIG. 3 has been performed to optimize the performance under a wide variety of conditions. Assuming that the flow of sea water through the HAE stones 78 obeys Darcy's Law, known in the art, and that the compression of the air pocket 94 in the upper chamber 50 follows the Ideal Gas Law, the differential equation for the absolute pressure inside the upper chamber 50 at the elevation 80 may be given as follows:

$$P_{au} + \frac{C}{P_{au}^2} P'_{au} = P_{awc} \quad (4)$$

where $P'_{au}$ is the time rate of change of $P_{au}$, C is a constant that depends on the size of the air pocket 94 in the upper chamber 50; the unit weight of sea water ($\gamma_s$); the permeability of the HAE stones 78 (k); and on the geometry of the HAE stones 78. All pressures in Equation (4) are absolute. The constant C has the following form:

$$C = \frac{P_o V_o \gamma_s l}{2kA} \quad (5)$$

where $P_o$ is the initial absolute pressure (101.4 kPa) upon assembly of the multi-sensor piezometer 12, $V_o$ is the initial volume (=1390 cc) of a typical air pocket 94 upon assembly of the multisensor piezometer 12, l is the typical length of the HAE stones 78 (1 cm), and A is the typical cross-sectional area of one HAE stone 78 (3.2 cm$^2$).

Figure 8:
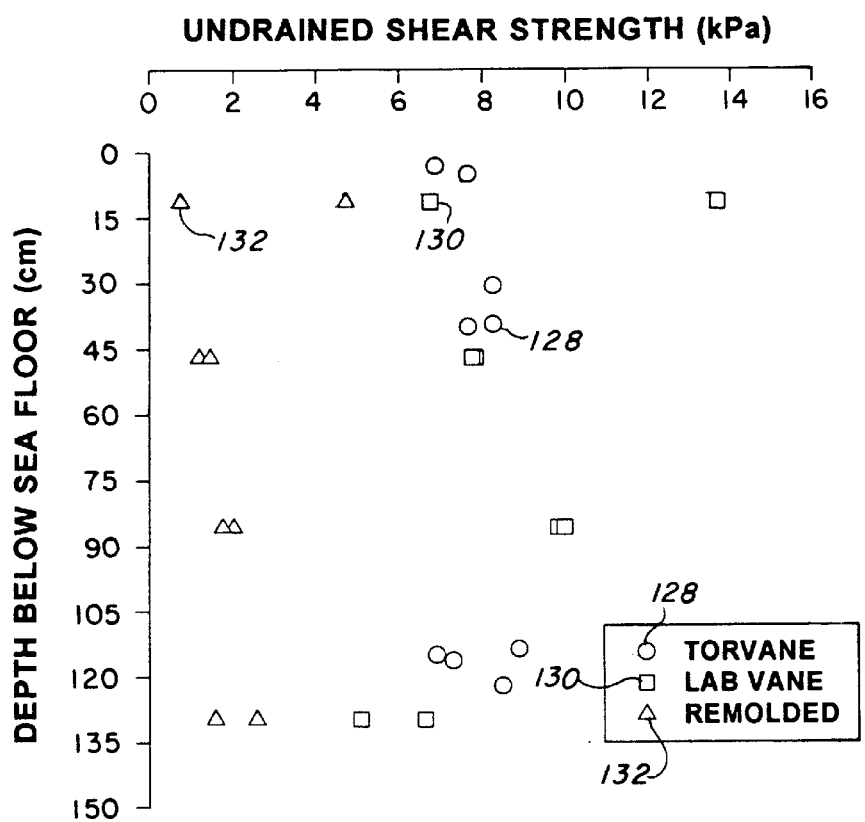
FIG. 8 is a plot of undrained shear strength from Tore Van and Lab miniature Vane tests as a function of depth below the sea floor.

Equation (4) is a nonlinear first-order differential equation. The nonlinearity is due to the nonlinear pressure/ volume relationship of the typical air pocket 94 $P_o V_o = P_l V_l$. It is possible to linearize the differential equation by approximating the pressure/volume relationship as a linear function for small changes in $P_u$. The governing equation for such a linear function can then be written as:

$$P_{au} + KP'_{au} = P_{awc} \qquad (6)$$

where $$K = \frac{C}{P_{au\,mean}^2} = \frac{P_o V_o \gamma_s l}{2kA P_{au\,mean}^2} \qquad (7)$$

and $P_{au\,mean}$ is the mean absolute pressure inside the typical upper chamber 50 at the elevation 80 of the HAE stones 78 that is assumed to remain constant over the time scale of the surface wave interaction measurements (186.4 kPa for a typical environment). A solution to this ordinary differential equation (ODE) can be found by making two simplifying assumptions regarding the form of the total pressure function. First, the typical total water column pressure ($P_{awc}$) is represented as the atmospheric pressure ($P_a$) plus the water pressure due to the average water depth from the center of the wave height to the elevation 80 of the HAE stones 78 ($Y_\gamma D$) (where D is shown as dimensional line 84 of FIG. 3) plus a perturbation due to a sinusoidal wave form (y) according to the following:

$$P_{awc} = P_a + \gamma_s(D + y) = P_a + \gamma_s \left( D + a \sin\left[ \frac{2\pi}{\lambda}(x - ct) \right] \right) \qquad (8)$$

where a is the wave amplitude, c is the wave celerity, D shown in FIG. 8 as distance 84, represents the average water depth from the HAE stones 78 to the center of the wave height, t is time, $\gamma_s$ is the specific weight of sea water, and $\Lambda$ is the wave length. Second, the wave celerity (c) under the assumptions of linear wave theory is expressed as:

$$c = \sqrt{\frac{g\lambda}{2\pi} \tanh\left( \frac{2\pi D}{\lambda} \right)} \qquad (9)$$

where g is gravity and all other variables have been previously defined.

When the origin is selected as x=0, these assumptions allow the ordinary differential equation (ODE) solution to be written as:

$$P_{au} = P_a + \gamma_s D + \frac{a\gamma}{b^2 K^2 + 1} [bKe^{-t/K} - bK\cos(bt) + \sin(bt)] \qquad (10)$$

where $$b = -2\frac{\pi}{\lambda} c = -\sqrt{2\frac{\pi}{\lambda} g \tanh\left( \frac{2\pi D}{\lambda} \right)} \qquad (11)$$

The solution to Equation (6) is not unique without making appropriate substitutions for the initial condition (t=0). The non-unique behavior stems from the exponential term, whereby any general constant not involving t may be used as a coefficient and still satisfy the homogeneous ODE. The coefficient shown in Equation (10) for the exponential term satisfies the ODE and assumes that the initial condition is that $P_{au} = P_{awc}$ at t=0. This initial condition is somewhat arbitrary since the imposed condition probably does not exist at t=0. The K is Equation (6) represents the dampening in the system. The lower the K the faster the exponential term will go to zero and the more rapidly the internal pressure within the typical chamber 50 will respond to the changes in external pressure. The K can be chosen so that the differential transducers $48_1$, $48_2$, $48_3$, $48_4$, $48_5$, and $48_6$ will respond only to events up to a certain cut off frequency. Thus, the magnitude of the K should be the primary consideration in designing similar systems. The magnitude of K may have a typical value of 1270 seconds. The total pressure measurement involved in the practice of the present invention may be further described with reference to FIG. 5.

Figure 5:
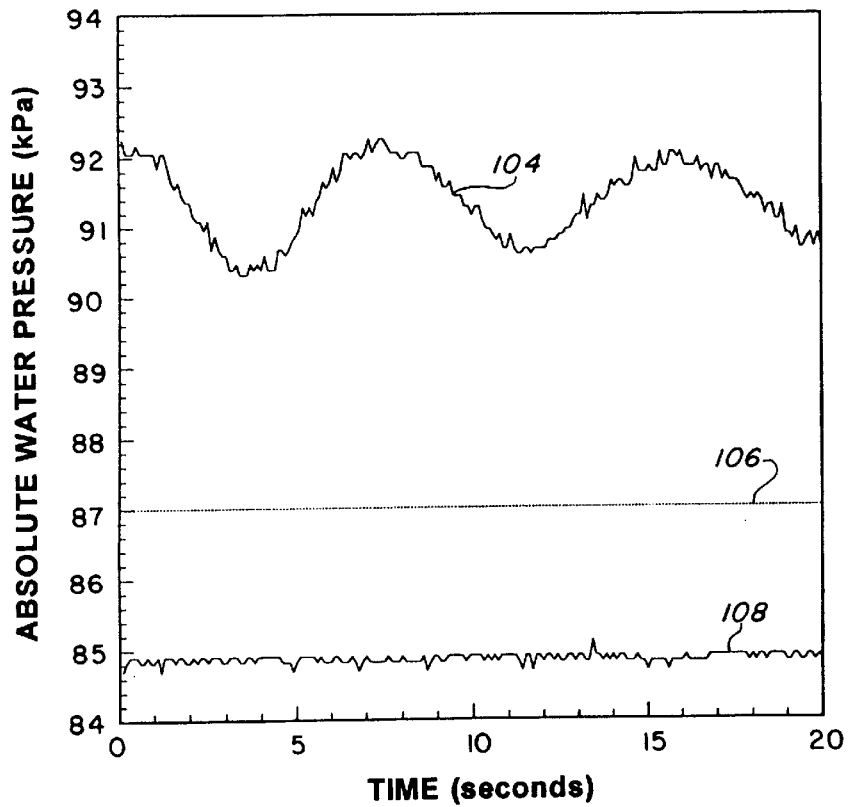
FIG. 5 is a plot illustration of a comparison of free water column pressure and measured and predicted inside upper chamber pressure (total pressure).

FIG. 5 illustrates three plots 104, 106 and 108 respectively representative of the free water column as measured by total pressure transducer 92, predicated inside typical chamber 50 pressure offset, and inside typical chamber 50 pressure as measured by the total pressure transducer 90. FIG. 5 presents the measured total pressure in the water column plot 104 (subtracting the atmospheric pressure $P_a$), the measured pressure inside upper typical chamber 50 plot 108, and the predicted total typical chamber 50 pressure plot 106 from Equation (10) during one of the insertions (i.e., the multi-sensor piezometer 12 insertions into the marine sediments) at a typical site of deployment. The outside total pressure transducer 92 is typically located approximately 0.6 m lower in the water column than the total pressure transducer 90 inside the upper typical chamber 50 and hence the 6 kPa offset between plots 104 and 108 of FIG. 5. In FIG. 5, the predicted internal pressure has been shifted to compare the cyclic response with the measured response of the inside total pressure transducer 90. Of primary interest is the cyclic response of the dampening system of the present invention. The cyclic component due to the surface waves has been removed and Equation (10) makes a good prediction of this response.

In the practice of this invention, the larger the constant K in Equation (7), the more efficient is the cyclic damping system. The cyclic damping system comprising the elements 68, 74, 78 and 94 of FIG. 3 is successfully filtering out the surface wave activity (20 cm waves in this instance with an 8.7 second period) so that the negative side response is flat and the differential pressure transducers $48_1 \ldots 48_6$ are measuring variations from the static water column pressure. The predicted response is consistent with the measured pressure inside the typical upper chamber 50. Equation (10) can be used to design other multi-piezometer probes that would be based on the same general principles of the present invention.

It should now be appreciated that the present invention 10 provides a multi-sensor piezometer 12 having a hydrodynamic dampening system (elements 68, 74, 78 and 94) that enable the precise measurements of bottom and sub-bottom pore pressures in spite of any surface wave activity.

DEPLOYMENT OF MULTI-SENSOR PIEZOMETER OF THE PRESENT INVENTION

The multi-sensor piezometer of the present invention can be deployed either on the Seafloor Lander System of FIG. 1 or tethered to the back of a ship. In each case, the following sequence of four (4) primary steps should be completed in order to evaluation system performance, assure the collection of valid data, and complete the experimental objectives.

1) Static Fluid Reservoir Calibration. Assemble the multi-sensor piezometer 12 and calibrate the pressure transducers using an adjustable static fluid reservoir. This calibration can be performed either in the laboratory or dockside prior to deployment.

2) Free Water Column Calibration Check. Check the calibration equations of each differential pressure transducers $48_1 \ldots 48_6$ while the probe 14 is suspended in the free water column prior to insertion in the marine sediment by comparing the predicted and measured mean differential pressures ($P_m$'S)

3) Probe Insertion and Pressure Dissipation. Insert the probe in the sediments and measure the transient pore water pressures.

4) Pore Pressure Response. Measure sediment pore water pressures and the corresponding free water column pressures under surface wave action.

Static Fluid Reservoir Calibration

The static fluid reservoir calibration procedure is as follows. The complete multi-sensor piezometer 12 is assembled. A plastic sleeve is placed over the probe shaft 14 to develop a closed chamber for system saturation. De-aired Fluorinert created by the covering sleeve is caused to flow from an upper reservoir or chamber 50 into the plastic sleeve, up the pressure transmission lines $46_1$, $46_2$, $46_3$, $46_4$, and $46_5$, and into the typical upper chamber 50 via conventional bleed screws on transducers $48_1$, $48_2$, $48_3$, $48_4$, and $48_5$ respectively. When each line is fully saturated, as evidenced by the lack of air bubbles coming from the positive side bleed screws of the differential transducers $48_1$, $48_2$, $48_3$, $48_4$, and $48_5$, the typical upper chamber 50 is placed at the level of the Fluorinert (fluid 68) inside the upper chamber 50 and the fluid pressures are allowed to equilibrate. The mechanical zeros (output voltages at zero differential pressure) of the transducers $48_1 \ldots 48_5$ are recorded and the positive side bleed screws are closed. The moveable fluid reservoir is then placed at different elevations using a calibration stand that has been graduated in, for example, 0.3048 m (1 ft.) increments and the changes in fluid pressure registered by each pressure transducer are recorded by the data acquisition system 24. The calibration is performed from roughly −30 kPa to +30 kPa (depending on the elevation of the probe 14 versus the calibration stand) in 5.6 kPa increments using at least 2 full cycles of measurement. Total pressures are estimated from the height of the moveable reservoir and the unit weight of the Fluorinert (1.86 g/cc at 25° C.). Linear regression analyses are performed on the resulting data and calibration equations are developed in terms of total pressure for each of the transducers $48_1 \ldots 48_5$ in the following form and which may be used to convert raw data into engineering units for subsequent analysis:

$$P_m = C_{f2} V_a + P_o \quad (12)$$

where $C_{f2}$ is the calibration factor with units of (kPa/volt), and $V_a$ is the actual voltage from each transducer according to Equation (1), and $P_o$ is the y-intercept. The other pressure transducers $48_6$, 90 and 92 are calibrated in a similar manner. Table 3 presents the typically derived regression constants for each of the transducers associated with the corresponding channels 1–8 previously described with reference to FIG. 4.

TABLE 3

Calibration Equation $P_m = C_{f2} V_m + P_o$

| Channel Number | Calibration Factor $C_{f2}$ (kPa/Volt) | y-intercept $P_o$ (kPa) | $r^2$ |
|---|---|---|---|
| 1 ($96_1$) | 6.3411 | 1.2470 | 0.9999 |
| 2 ($96_2$) | 8.7583 | −5.6438 | 0.9999 |
| 3 ($96_3$) | 9.0902 | 0.7041 | 0.9999 |
| 4 ($96_4$) | 6.9699 | 8.6187 | 0.9999 |
| 5 ($96_5$) | 6.3692 | 5.1004 | 0.9999 |
| 6 ($96_6$) | 9.1662 | −3.8431 | 0.9999 |
| 7 ($96_7$) | 40.3456 | 7.2786 | 0.9996 |
| 8 ($96_8$) | 41.5538 | 0.2161 | 0.9999 |

Free Water Column Calibration Check

During deployment, while the multi-sensor piezometer 12 is suspended in the free water column prior to insertion, it is possible to check the calibration equations for each of the five probe-shaft differential pressure transducers $48_1$, $48_2$, $48_3$, $48_4$, and $48_5$. The measured differential pressure is a function of the total pressure at the elevation of the corresponding porous stones $16_1$, $16_2$, $16_3$, $16_4$ and $16_5$, the total pressure inside the typical upper chamber 50, the depth of the sea water between the HAE stones 78 and the top (that is boundary 72 of FIGS. 2 and 3) of the Fluorinert (fluid 68) inside the typical upper chamber 50, and the total combined length of Fluorinert ($d_2+d_3$) assuming complete saturation. Refer to FIG. 3. At this stage of the deployment the pressure relief valve 58 on top of the chamber 50 is open to allow for rapid equilibration of internal pressures. Considering the mean depth of the multi-sensor piezometer 12 to the HAE stones 78 (see distance 84 of FIG. 3) and that the $P_u$ (total pressure inside the typical upper chamber 50 at the HAE stones 78) is equal to $P_{wc}$ (water column pressure) because the pressure transfer valve of relief valve 58 is open, Equation (2) can be written in terms of mean value of $P_m$ (average of measured differential pressure) in the following form:

$$\overline{P}_m = (d_2 + d_3)(\gamma_s - \gamma_f) \quad (13)$$

where all of the terms have been previously defined.

According to Equation (13), the mean measured pressure for each of the five differential transducers $48_1$, $48_2$, $48_3$, $48_4$, and $48_5$ while the multi-sensor piezometer 12 is suspended in the free water column is fixed by the total length Fluorinert (fluid 68) in the system and the difference in the units weight of sea water and Fluorinert. The measured pressure of each differential transducer may be further described with reference to FIG. 6.

Figure 6:
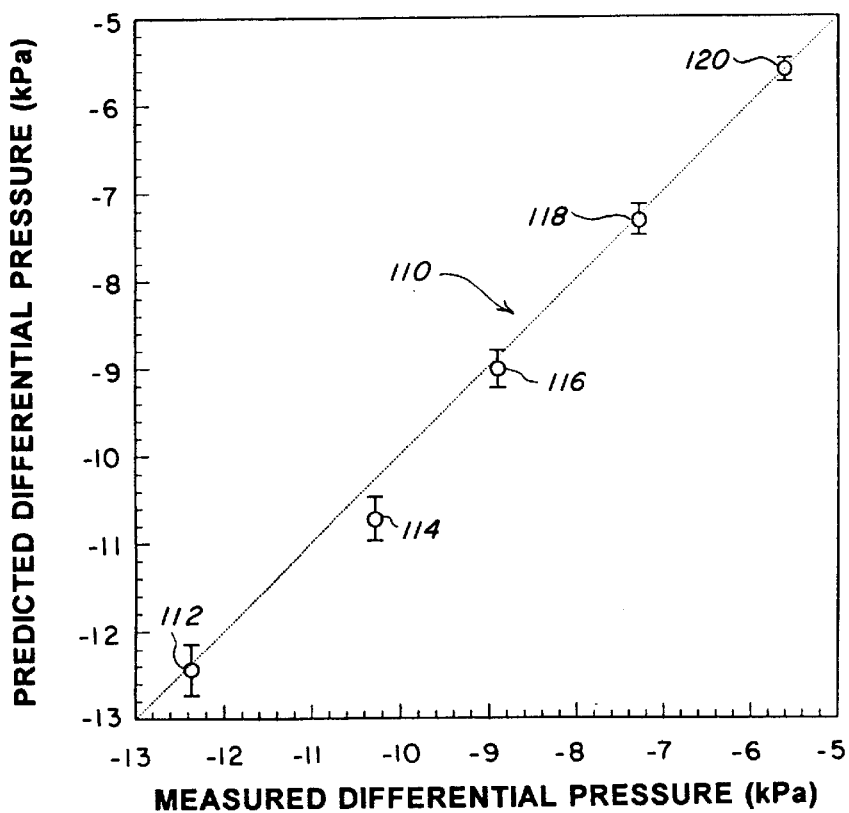
FIG. 6 is a plot of measured versus predicted mean differential pressure for multi-sensor piezometer in the free water column prior to insertion.

FIG. 6 illustrates a prediction curve 110 associated with the data of channels 1, 2, 3, 4 and 5 (see FIG. 4 data acquisition system 24) respectively identified by symbol having reference number 112, 114, 116, 118 and 120. The plot 110 of FIG. 5 represents measured versus predicted differential pressure for the five probe differential transducers $48_1$(112), $48_2$(114), $48_3$(116), $48_4$(118), and $48_5$(120) prior to the first insertion during a deployment. With the exception of Channel 2 (114), the measured mean differential pressures are within 0.2 kPa of the predicted values (plot 110). The measured mean differential pressure on Channel 2 (114) is 0.5 kPa higher than the predicted value. This difference could indicate the presence of an air bubble in the pressure transmission line $46_2$ was such that the actual combined length of Fluorinert is less than $d_2+d_3$. Because of the low viscosity of the Fluorinert, the presence of an air bubble in the pressure transmission line $46_2$ of Channel 2 (differential pressure transducer $48_2$) should not materially affect the response of the transducer to cyclic effects. Ranges in predicted pressure have been placed on FIG. 6 to indicate how changes in $\gamma_f$ due to a +10° C. change in temperature could affect the comparison between measured and predicted values. The coefficient of thermal expansion for Fluorinert FC-40 is 0.0012 ml/ml °C. FIG. 6 indicates that the multi-sensor piezometer 12 (with the use of the inside absolute pressure transducer 90) is capable of detecting total pressures with an approximate accuracy of 0.2 kPa in the absence of air bubbles in the pressure transmission lines, such as $46_1 \ldots 46_5$.

Probe Insertion and Pressure Dissipation

The multi-sensor piezometer 12 is preferred to be inserted rapidly into fine-grained sediments using a free-fall technique driven by lead weights 34 (see FIG. 1) attached above the multisensor piezometer 12. In one deployment, 90.7 kg (200 lbs) of lead weights were used to drive the insertion of the multi-sensor piezometer 12 into the marine sediments 40. Upon full insertion of the probe, the weights are typically removed using a second tetherline and the excess pore pressure dissipation rates are monitored. Estimates of in situ permeability and undrained shear strength can be developed from the pore pressure dissipation data using a technique more fully explained by Bennett et al in the technical article "In Situ Undrained Shear Strengths and Permeabilities Derived from Piezometer Measurements," Strength Testing of Marine Sediments: Laboratory and In Situ Measurements, R. C. Chaney and K. R. Demars, Editors, published in the *American Society for Testing Materials, Special Testing Publication* 883, 1985b, pp. 83–100, the entirety of which is incorporated herein by reference for all purposes.

Gravity core samples (7.6 cm diameter) were collected at a deployment site in order to classify the soils and to determine various soil properties. Soil classifications were performed on the fourth core according to the Unified Soil Classification System. Grain size analyses were conducted in general accordance with ASTM D 422-63 and Atterberg limit determinations were conducted in general accordance with ASTM D - - - . The soils were a heterogeneous mix of greenish grey Clayey Sand (SC) and greenish grey Sandy Lean Clay (CL) with some shell fragments. The results of such testing may be described with reference to FIG. 7.

Figure 7:
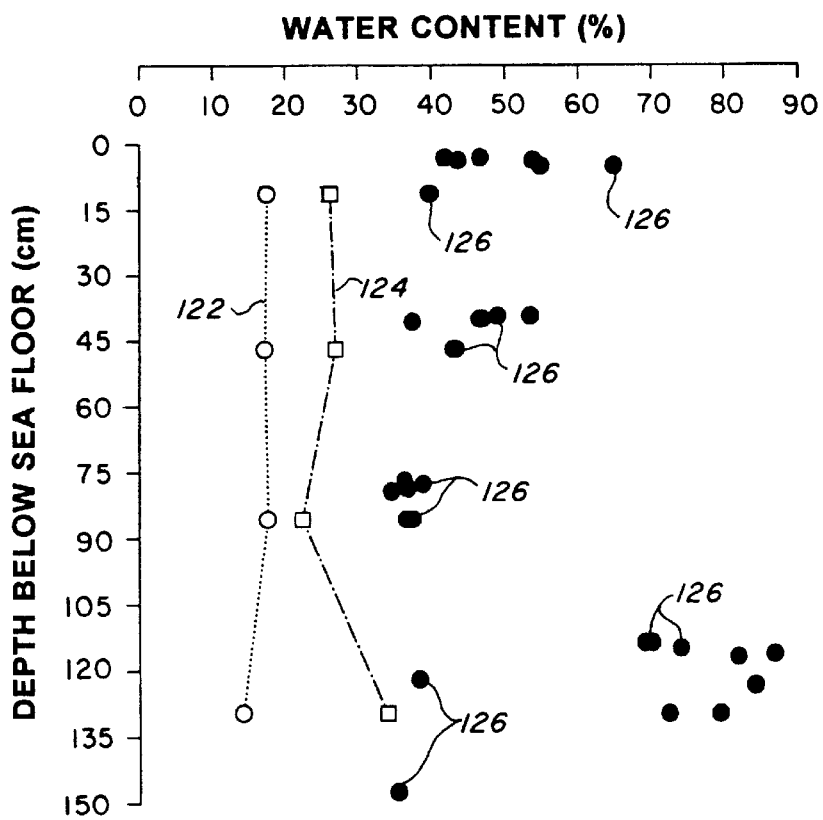
FIG. 7 is a plot of natural water content compared to Atterberg Limits.

FIG. 7 illustrates two plots 122 and 124 respectively representative of the plastic limit and liquid limit, sometimes referred to as Atterberg limits, related to the sediment 40 (see FIG. 1) and water interface. FIG. 7 further illustrates a plurality of dots 126 representative of natural water content. FIG. 7 presents the measured Atterberg limits (plots 122 and 124) and the natural water content (dots 126) as a function of depth below the sediment/water interface. In all instances, the natural water content (dots 126) is higher than the liquid limit 124. The specific gravity was determined in general accordance to ASTM 854-83, and ranged from 2.59 to 2.62. Worm holes were prevalent in the upper 10 to 20 cm of the core of the sediment.

The undrained shear strength of the soil was estimated with a Torvane and a lab miniature vane on the more cohesive portions of the sediments, in general conformance to ASTM D - - - and ASTMD - - - , respectively. Remolded lab vane tests were also conducted to obtain an indication of the sensitivity of the material and the results of such testing may be further described with reference to FIG. 8.

FIG. 8 illustrates a plurality of three different symbols identified with reference numbers 128, 130 and 132 and indicative of sensitivities respectively known in the art as Torvane, Lab Vane and Remolded. FIG. 8 presents the undrained and remolded shear strengths as a function of depth below the sediment/water interface. The undrained shear strength is less than 14 kPa in all tests and the sensitivity ranges from 2.6 to 9.

Figure 9:
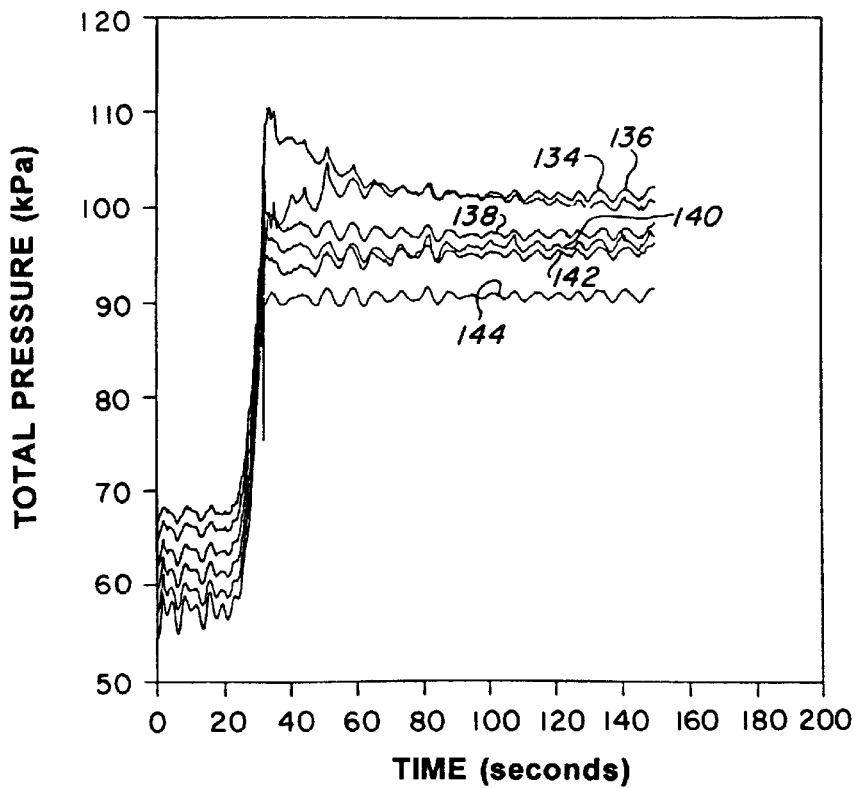
FIG. 9 is a plot of measured pore water pressures upon the first insertion of the multi-sensor piezometer.

FIG. 9 presents the pore pressure dissipation data from the first insertion of the multi-sensor piezometer 12 the deployment site for each of the five pore pressure measurement locations, that is, those identified by the locations of porous stones $16_1$, $16_2$, $16_3$, $16_4$ and $16_5$ in marine sediment 40. FIG. 9 illustrates six plots, 134, 136, 138, 140, 142 and 144 respectively yielded by the data applied to channels 1, 2, 3, 4, 5 and 7 (transducers $48_1$, $48_2$, $48_3$, $48_4$, $48_5$ and 92 respectively) of the data acquisition system 24 of FIG. 4. The data are presented in terms of the total pressure measured at the porous stone locations in accordance with Equation (2). All channels (1, 2, 3, 4, 5 and 7) show a rapid rise in total water pressure that is attributed to the rapid descent of the multi-sensor piezometer 12 in the water column during insertion. After this initial rise, three of the porous stones (Channels 2, 3, 4) registered a gradual decrease in pore pressure (dissipation of excess pore pressure). The pressure decrease on Channels 3 and 4 was slight compared to Channel 2. Two of the porous stones $16_1$ and $16_5$ registered a gradual build up of pore water pressure after insertion (Channels 1 and 5). While it is not known exactly, it is believed that this phenomena may be due to heterogeneity in the sediments. There are zones of high permeability where some excess pressures are rapidly dissipated and zones of low permeability where pore pressure may build up under time-dependent settlement effects due to surface loading of the probe 14 body.

Pore Pressure Response

Figure 10:
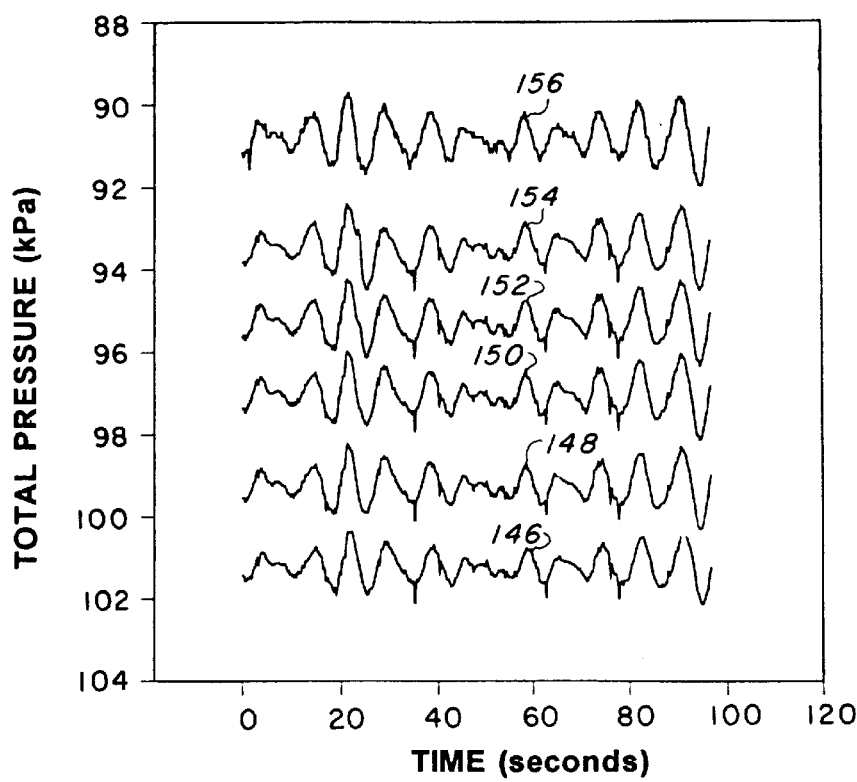
FIG. 10 is a plot of pore water pressure response to cyclic wave effects.
Figure 11:
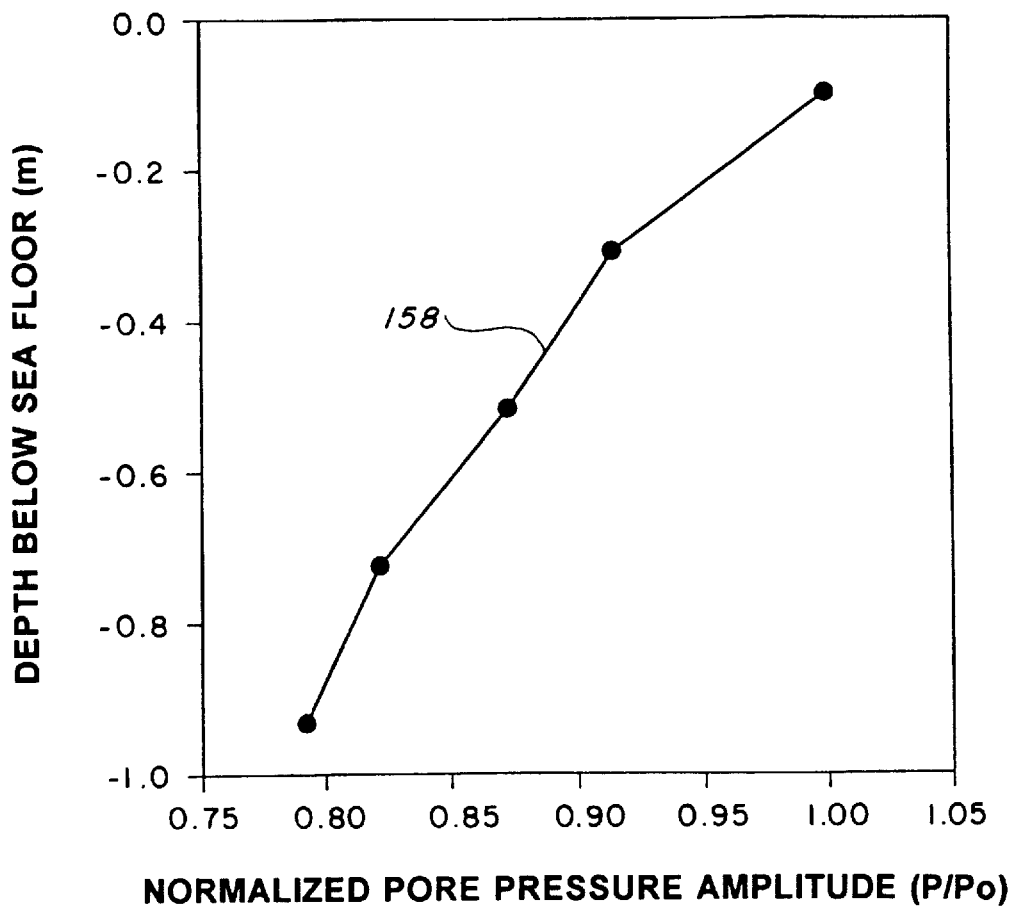
FIG. 11 is a plot of normalized pore pressure amplitude as a function of depth below the sea floor.

After the pore water pressures have equilibrated to their steady state values, the multi-sensor piezometer 12 is commonly left in the sediments and the pore pressure response to surface waves is monitored. During this phase of the deployment, the amplitude of the pore pressure response as a function of depth below the sea floor and the phase lag as a function of depth are of particular interest. FIG. 10 is a time history, represented by plots 146, 148, 150, 152, 154 and 156 (channels 1, 2, 3, 4, 5 and 7), of the total pressure in the free water column and along the probe shaft for a portion of time during the first insertion. There is no apparent phase lag in these data. FIG. 11 is a plot 158 of the normalized pore pressure amplitude (amplitude of pore pressure response at a particular depth in the sediments divided by the amplitude of the water column pressure) versus depth in the sediments for one surface wave with a 0.99 kPa amplitude and an 8.7 second period. There is a clear pressure attenuation with depth. The pore pressure amplitude at a point approximately 1 m below the surface is 80% of the surface value.

It should now be appreciated that the present invention provides a multi-sensor piezometer 12 for shallow marine sediments having a primary function to collect pore pressure data under the action of surface waves for a wide variety of marine sediments. These types of data are essential for understanding the fundamental mechanisms that control the generation of pore pressures in marine sediments.

It should be further appreciated that the multi-sensor piezometer 12 of the present invention has been described and the physical equations that govern its response under laboratory and field conditions have been derived. The multi-sensor piezometer 12 utilizes variable reluctance type differential pressure transducers in conjunction with total pressure transducers and an innovative cyclic damping system to measure small changes in pore water pressures at various selectable depths below the sea floor (the maximum depth investigated thus far is 0.93 m). Fluorinert FC-40 fluid serving as fluid 68 of FIGS. 2 and 3 is used as the exemplary primary pressure transmission medium for the system.

A sequence of steps have been outlined for validating the measurements and collecting the relevant data. These include: calibration of the pressure transducers using a moveable static fluid reservoir; assessment of system performance in the free water column prior to insertion; the measurement of transient response immediately after insertion of the probe; and the measurement of the log term response under surface wave activity.

Insertion data derived by the practice of the present invention has been presented to show a typical transient response for fine grained marine sediments (FIG. 9). The pore pressure response to surface wave activity has been presented in terms of time histories and normalized pore pressure amplitude versus depth below the sea floor. These data indicate that there is little or no phase delay in the pore pressure response at a typical deployment site (FIG. 10). There is a 20% reduction in the pore pressure amplitude for a 0.99 kPa surface wave with a period of 8.7 seconds at approximately 1 m below the sea floor (FIG. 11).

It should further be thoroughly understood that many modifications and variations of the present invention are possible within the purview of the claimed invention. It is therefore to be understood that, within the scope of the appended claims, the invention may be practiced otherwise than as specifically described.

What I claim is:

1. A piezometer for measuring pore water pressure in marine sediments comprising:

(a) a tubular shaft having one end that is tapered, said tubular shaft housing a plurality of first porous stones that are spaced apart from each other by a first distance and connected to one end of a tube;

(b) a first chamber connected to the other end of said tubular shaft and having entrance portions;

(c) a plurality of differential pressure transducers housed in said first chamber, one for each of said first porous stones and each having positive and negative pressure inputs and providing an output signal proportional to the difference between the positive and negative pressure inputs, each of said plurality of differential transducers having its positive input connected to the other end of said tube of its respective first porous stone;

(d) a fluid having a density greater than sea water and of a sufficient amount to immerse said plurality of differential pressure transducers when placed in said first chamber;

(e) second porous stones disposed in said entrance portions of said first chamber and adapted to allow sea water to enter therethrough to form a pocket of sea water floating on said fluid of said first chamber; and (f) a pocket of air confined in said first chamber and trapped above said pocket of sea water.

2. The piezometer according to claim 1 further comprising a second chamber interposed between said first chamber and said other end of said tubular shaft.

3. The piezometer according to claim 1, wherein said first chamber has a top portion and wherein said piezometer further comprises a relief valve having an entrance portion at said top portion of said first chamber exposed to ambient and an exit portion in said pocket of sea water.

4. The piezometer according to claim 1 further comprising:

a first absolute pressure transducer housed in said first chamber; and a second absolute pressure transducer lodged on the outside of said first chamber.

5. The piezometer according to claim 1 further comprising another differential pressure transducer housed in said first chamber and also being in fluid communication between its positive pressure input and ambient.

6. The piezometer according to claim 1, wherein said fluid has a surface tension of about 16 dynes/cm and a viscosity of about 2.4 centistokes.

7. The piezometer according to claim 5, wherein said differential pressure transducers have a variable reluctance.

8. The piezometer according to claim 1, wherein each of said plurality of first porous stones has a pore size of from about 0.23 mm to about 0.29 mm, a permeability of between about 1.7 to $1.0 \times 10^{-1}$ cm/sec., and a porosity of about between 35 to 40%.

9. The piezometer according to claim 1, wherein said first distance is about 0.208 m beginning about 0.1 m below the first chamber.

10. The piezometer according to claim 1, wherein each of said second porous stones is an HAE stone.

* * * * *